(12) United States Patent
Fan

(10) Patent No.: US 12,310,919 B2
(45) Date of Patent: May 27, 2025

(54) STORAGE CASE AND MASSAGER SYSTEM

(71) Applicant: SHENZHEN KOVIDA MEDICAL PRODUCTS CO., LTD., Shenzhen (CN)

(72) Inventor: Meilan Fan, Shenzhen (CN)

(73) Assignee: SHENZHEN KOVIDA MEDICAL PRODUCTS CO., LTD., Shenzhen (CN)

( * ) Notice: Subject to any disclaimer, the term of this patent is extended or adjusted under 35 U.S.C. 154(b) by 0 days.

(21) Appl. No.: 18/639,989

(22) Filed: Apr. 19, 2024

(65) Prior Publication Data

US 2024/0350349 A1    Oct. 24, 2024

(30) Foreign Application Priority Data

Apr. 20, 2023  (CN) .......................... 202320971141.2

(51) Int. Cl.
*A61H 9/00* (2006.01)
*A61L 2/10* (2006.01)

(52) U.S. Cl.
CPC .............. *A61H 9/0057* (2013.01); *A61L 2/10* (2013.01); *A61H 2201/0157* (2013.01); *A61H 2201/0161* (2013.01); *A61L 2202/11* (2013.01)

(58) Field of Classification Search
CPC .......... A61H 9/0057; A61H 2201/0157; A61H 2201/0161; A61H 19/00; A61H 19/30; A61H 19/32; A61H 19/34; A61H 19/40; A61H 19/44; A61H 19/50; A61L 2/10; A61L 2202/11
See application file for complete search history.

(56) References Cited

U.S. PATENT DOCUMENTS

| 9,717,809 | B2* | 8/2017 | Martz | H02J 7/0042 |
| 2004/0025899 | A1* | 2/2004 | Pinsky | A45D 44/18 |
| | | | | 132/310 |
| 2014/0319374 | A1* | 10/2014 | Chandler | A61L 2/10 |
| | | | | 250/455.11 |
| 2015/0313354 | A1* | 11/2015 | Mongan | A61L 2/24 |
| | | | | 15/105 |
| 2016/0302567 | A1* | 10/2016 | Gorelick | A46B 17/065 |
| 2020/0315339 | A1* | 10/2020 | Guo | A46B 13/008 |
| 2021/0052463 | A1* | 2/2021 | Lenke | A61H 19/34 |
| 2021/0153638 | A1* | 5/2021 | Jeong | A47K 7/043 |
| 2022/0087896 | A1* | 3/2022 | Tai | A61H 23/02 |
| 2023/0053031 | A1* | 2/2023 | Shamir | A61L 2/28 |

FOREIGN PATENT DOCUMENTS

CN            109998893 A   *   7/2019   ............. A61F 7/007

\* cited by examiner

*Primary Examiner* — Tu A Vo
*Assistant Examiner* — Kelsey E Baller

(57) ABSTRACT

A storage case includes a base, a circuit board, and an ultraviolet lamp. A storage groove is defined in one side of the base. The storage groove is configured to accommodate the suction massager. A mounting cavity is formed in the base. A first opening is defined in a groove wall of the storage groove to communicate the storage groove with the mounting cavity. The circuit board is mounted in the mounting cavity. The ultraviolet lamp is electrically connected to the circuit board. The ultraviolet lamp is mounted at the first opening of the storage groove, so that the ultraviolet lamp emits ultraviolet rays towards the storage groove. When the ultraviolet rays shine on the suction massager, bacteria lose vitality and are unable to grow or reproduce, thereby ensuring the physical health of the user.

8 Claims, 8 Drawing Sheets

STORAGE CASE AND MASSAGER SYSTEM

TECHNICAL FIELD

The present disclosure relates to a field of massaging devices, and in particular to a storage case and a massager system.

BACKGROUND

A suction massager is a massage device that generates negative pressure through a pressure field generating mechanism, thereby providing a suction sensation to a user and promoting blood circulation of the user.

When the user finishes using the suction massager, the user needs to fully clean the suction massager. The cleaned suction massager needs to be placed in a clean environment, otherwise bacteria are easy to breed, which has a negative impact on physical health of the user.

However, after investigation, it is found that a cleaning methods of suction massagers by users are generally relatively simple and a cleaning time is relatively short. After cleaning, the suction massagers are generally accommodated in storage bags, and the users also do not have a habit of regularly cleaning or replacing their storage bags, which cause the suction massagers to breed a large number of bacteria, seriously threatening physical health of the users.

SUMMARY

A technical problem to be solved by embodiments of the present disclosure is to provide a storage case and a massager system to solve a problem in the prior art that users have poor cleaning and storage habits, so that the suction massager breeds a large number of bacteria, seriously threatening physical health of the users.

In a first aspect, the present disclosure provides the storage case. The storage case comprises a base, a circuit board, and an ultraviolet lamp. A storage groove is defined in one side of the base. The storage groove is configured to accommodate the suction massager. A mounting cavity is formed in the base. A first opening is defined in a groove wall of the storage groove to communicate the storage groove with the mounting cavity. The circuit board is mounted in the mounting cavity. The ultraviolet lamp is electrically connected to the circuit board. The ultraviolet lamp is mounted at the first opening of the storage groove, so that the ultraviolet lamp emits ultraviolet rays towards the storage groove.

Furthermore, the storage case further comprises a first battery and a first charging structure. The first battery is mounted in the mounting cavity and is electrically connected to the ultraviolet lamp through the circuit board. The first charging structure is exposed on an outer sidewall of the base. The first charging structure is electrically connected to the first battery through the circuit board to charge the first battery.

Furthermore, the storage case further comprises second charging structures. A first end of each of the second charging structures is exposed on the groove wall of the storage groove, and a second end of each of the second charging structures is electrically connected to the first battery through the circuit board, so that the second charging structures are allowed to charge the suction massager.

Furthermore, the second charging structures are spring pins.

Furthermore, the storage case further comprises third charging structures. A first end of each of the third charging structures is exposed on the outer sidewall of the base, and a second end of each of the third charging structures is electrically connected to the first battery through the circuit board, so that the third charging structures are allowed to charge an external electronic device.

Furthermore, a control module is disposed on the circuit board, and the control module is configured to control the ultraviolet lamp to work for a predetermined time when the second charging structures charge the suction massager.

Furthermore, the storage case further comprises a travel switch or an electromagnetic induction switch. The travel switch or the electromagnetic induction switch is electrically connected to the ultraviolet lamp. After the travel switch or the electromagnetic induction switch is triggered, the ultraviolet lamp works for a predetermined time; the travel switch or the electromagnetic induction switch is triggered when the suction massager is accommodated in the storage case.

In a second aspect, the present disclosure provides a massager system. The massager system comprises a suction massager and the storage case mentioned above. The suction massager comprises a main body and a flexible massage piece mounted on the main body.

The storage groove is configured to accommodate the suction massager.

Furthermore, a shape of the storage case is matched with a shape of the suction massager, and the ultraviolet lamp of the storage case faces the flexible massage piece of the suction massager.

Furthermore, the main body comprises a pressure field generating mechanism. The pressure field generating mechanism comprises a chamber, a power assembly, and an output piece. The output piece is configured as at least a part of a chamber wall of the chamber. The power assembly is connected to the output piece, and the power assembly is configured to push the output piece to move or deform, so as to change a volume of the chamber. The chamber defines a second opening.

The flexible massage piece comprises a contact portion and a recessed portion. The contact portion is configured to contact a human body. The recessed portion is disposed on a central position of the contact portion. The recessed portion defines a recessed cavity. A flexible film is disposed on a bottom portion of the recessed cavity. The flexible massage piece is mounted on the second opening of the chamber. The recessed portion extends into the chamber from the second opening of the chamber to seal the chamber. When the volume of the chamber changes, a pressure difference formed on two sides of the flexible film causes the flexible film to deform to change the volume of the recessed cavity.

In a third aspect, the present disclosure provides a massager system. The massager system comprises a suction massager, the storage case mentioned above, and a vibration massager.

The suction massager comprises a main body and a flexible massage piece mounted on the main body.

The storage groove is configured to accommodate the suction massager. The vibration massager comprises a motor, a vibrator driven by the motor, and a second battery disposed therein.

The second battery is electrically connected to the motor. Fourth charging structures are exposed on a surface of the vibration massager. The fourth charging structures are electrically connected to the second battery. The fourth charging structures are connected to the third charging structures of the storage case to charge the second battery.

Compared with the prior art, the storage case of the present disclosure comprises the base, the circuit board, and the ultraviolet lamp. The storage groove is defined in the one side of the base. The storage groove is configured to accommodate the suction massager. The mounting cavity is formed in the base. The first opening of the storage groove is defined in a groove wall of the storage groove to communicate the storage groove with the mounting cavity. The circuit board is mounted in the mounting cavity. The ultraviolet lamp is electrically connected to the circuit board. The ultraviolet lamp is mounted at the first opening of the storage groove, so that the ultraviolet lamp emits ultraviolet rays towards the storage groove. When the ultraviolet rays shine on the suction massager accommodated in the storage case, DNA and RNA structures of the bacteria on the suction massager are destroyed, causing the bacteria to lose vitality and unable to grow or reproduce. Namely, by storing the suction massager in the storage case of the present disclosure, the number of the bacteria on the suction massager is effectively reduced, thereby ensuring the physical health of the user.

BRIEF DESCRIPTION OF DRAWINGS

Specific implementations of the present disclosure are further described in detail below in conjunction with accompanying drawings and embodiments. In the drawing.

Figure 1:
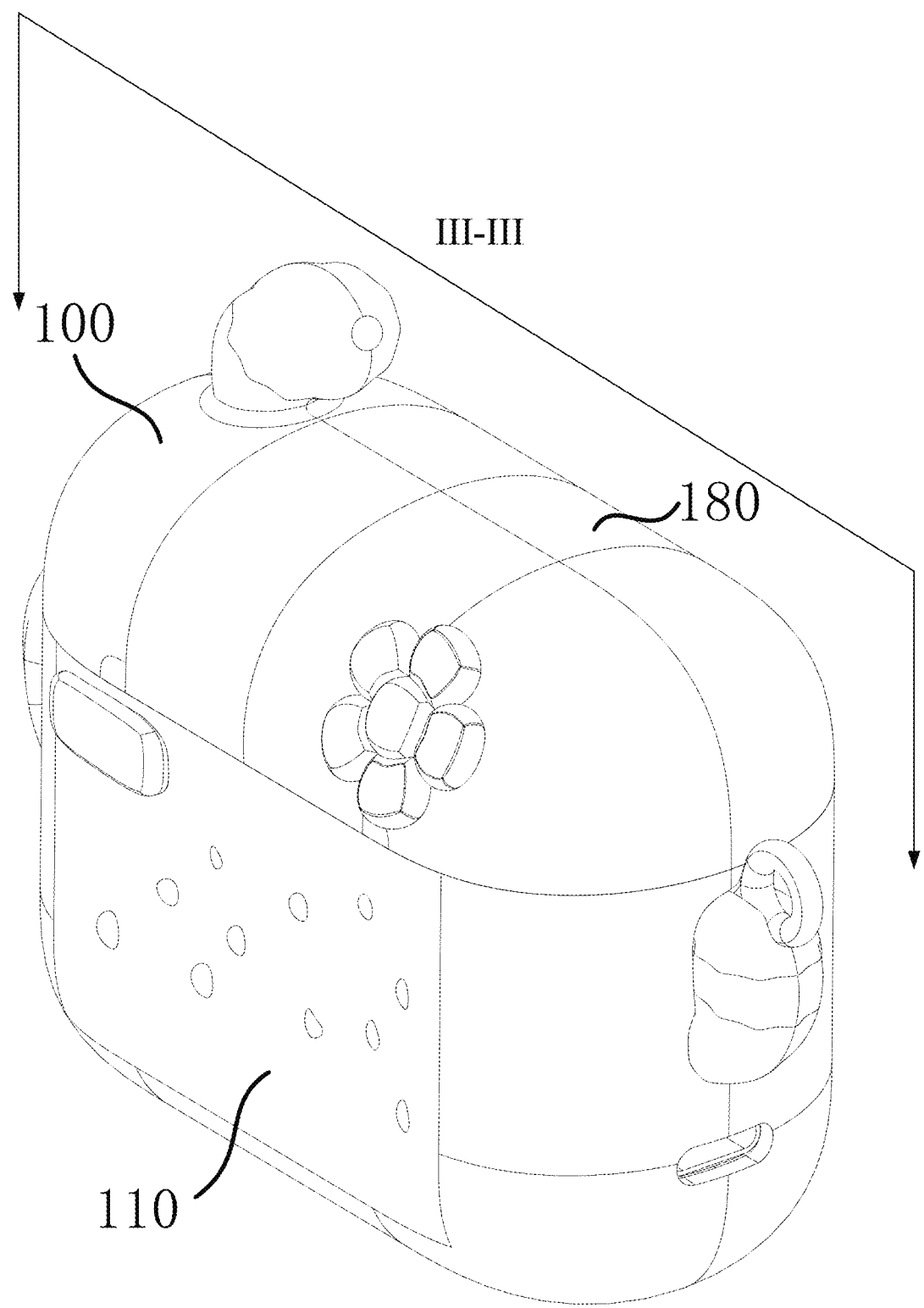
FIG. 1 is a perspective schematic diagram of a storage case according to one embodiment of the present disclosure.

Reference number in the drawings:
1000—massager system; 100—storage case; 110—base; 111—storage groove; 112—mounting cavity; 113—first opening; 120—circuit board; 130—ultraviolet lamp; 140—first battery; 150—first charging structure; 160—second charging structure; 170—third charging structure; 180—cover; 200—suction massager; 210—main body; 211—pressure field generating mechanism; 2111—chamber; 21111—second opening; 2112—power assembly; 21121—rotating driving piece; 211211—rotating shaft; 21122—eccentric rod; 211221—mounting portion; 211222—eccentric portion; 2113—output piece; 220—flexible massage piece; 221—contact portion; 222—recessed portion; 2221—recessed cavity; 223—flexible film; 250—fifth charging structure; 260—third battery; 300—vibration massager; 310—motor; 320—vibrator; 330—fourth charging structure; 340—second battery.

DETAILED DESCRIPTION

It should be noted that embodiments, implementations and related technical features of the present disclosure can be combined and replaced with each other without conflict. Optional embodiments of the present disclosure are described in detail with reference to the accompanying drawings.

Embodiments of the present disclosure provides a storage case 100. As shown in FIGS. 1-4, the storage case 100 comprises a base, a circuit board 120, and an ultraviolet lamp 130. A storage groove 111 is defined in one side of the base 110. The storage groove 111 is configured to accommodate a suction massager 200. A mounting cavity 112 is formed in the base 110. A first opening 113 is defined in a groove wall of the storage groove 111 to communicate the storage groove 111 with the mounting cavity 112. The circuit board 120 is mounted in the mounting cavity 112. The ultraviolet lamp 130 is electrically connected to the circuit board 120. The ultraviolet lamp 130 is mounted at the first opening 113 of the storage groove 111, so that the ultraviolet lamp 130 emits ultraviolet rays towards the storage groove 111.

Specifically, a user is able to use the storage case 100 to store the suction massager 200 by placing the suction massager 200 in the storage groove 111 of the base 110. Since the ultraviolet lamp 130 is mounted at the first opening 113 defined in the groove wall of the storage groove 111 and the ultraviolet lamp 130 is able to emit the ultraviolet rays toward the storage groove 111, when the ultraviolet rays shine on the suction massager 200 accommodated in the storage case 100, DNA and RNA structures of the bacteria on the suction massager 200 are destroyed, causing the bacteria to lose vitality and unable to grow or reproduce.

Namely, in the embodiment of the present disclosure, the storage case 100 accommodates the suction massager 200 while sterilizing the suction massager 200 through the ultraviolet rays, which effectively reduces the number of the bacteria on the suction massager 200, thereby ensuring physical health of the user.

Figure 2:
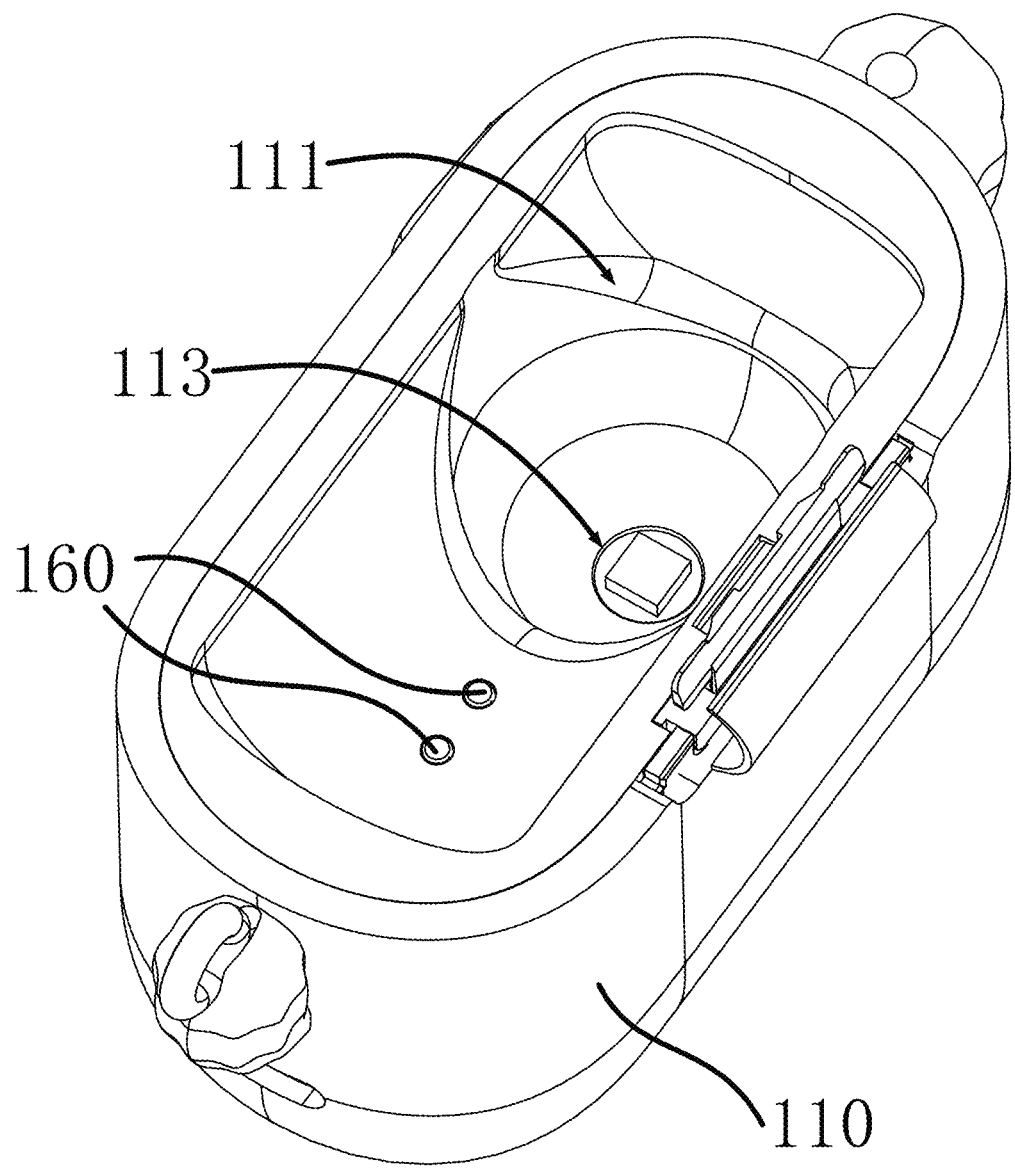
FIG. 2 is a perspective schematic diagram of a base, an ultraviolet lamp, and second charging structures according to one embodiment of the present disclosure.
Figure 3:
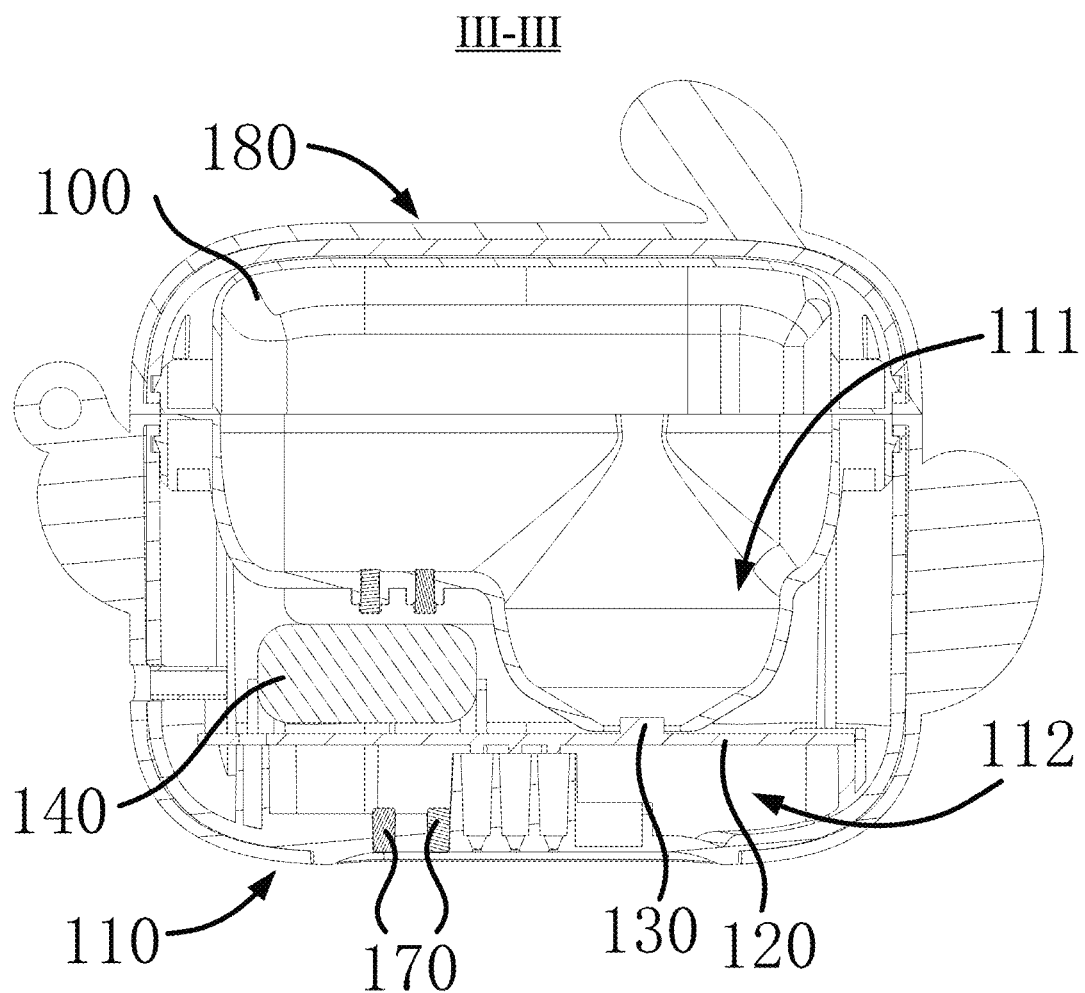
FIG. 3 is a cross-sectional schematic diagram of the storage case shown in FIG. 1 taken along a line III-III, according to one embodiment of the present disclosure.

As shown in FIGS. 2 and 3, in one specific embodiment, the circuit board 120 abuts against one side of the first opening 113 of the storage groove 111 close to the mounting cavity 112, and the ultraviolet lamp 130 is directly welded to a position where the circuit board 120 is exposed at the first opening 113 of the storage groove, so that the circuit board 120 blocks the first opening 113 to seal the mounting cavity 112, and external dust or other pollutants are prevented from entering the mounting cavity 112 from the first opening 113. Optionally, a sealing ring is bonded on a position where the first opening 113 abuts against the circuit board 120, so as to improve sealing performance.

Figure 4:
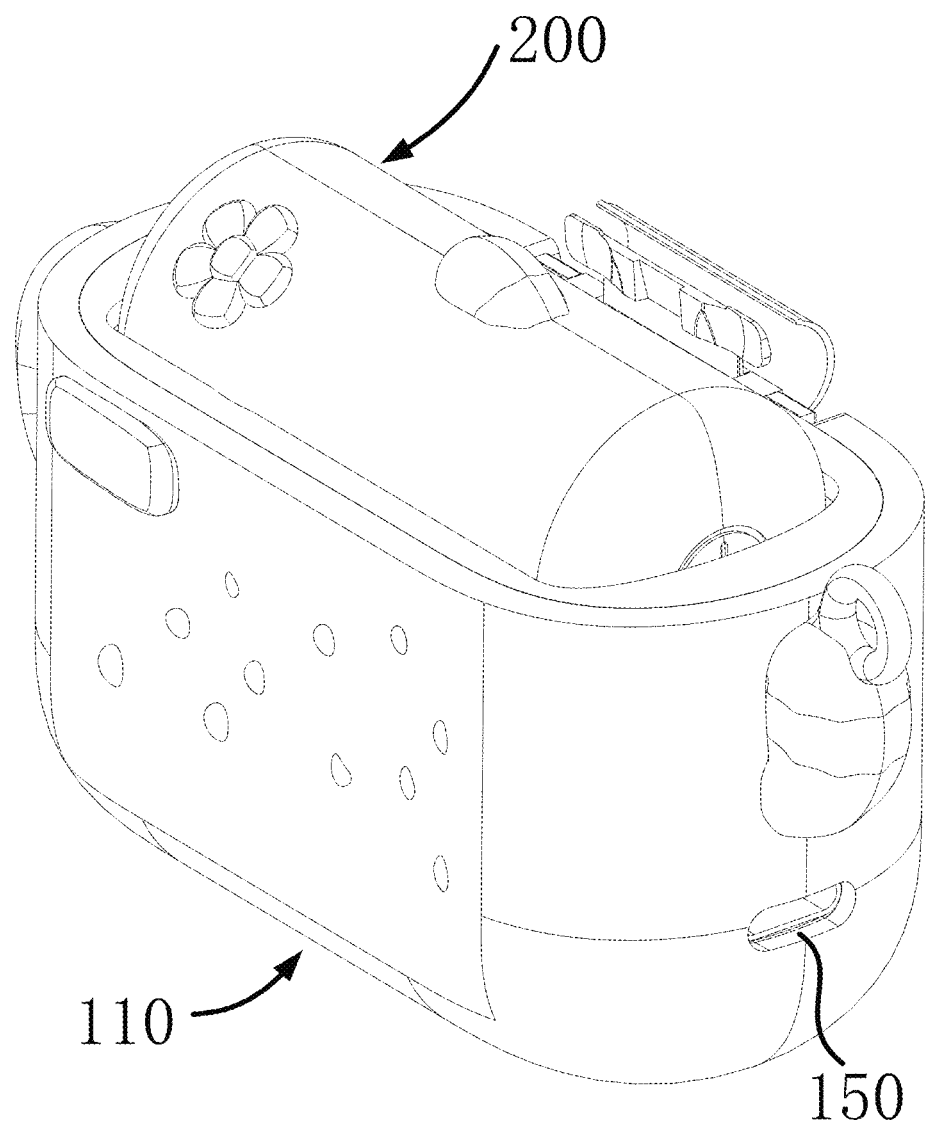
FIG. 4 is a perspective schematic diagram showing that a suction massager is accommodated in a storage groove according to one embodiment of the present disclosure.

As shown in FIGS. 3 and 4, in one specific embodiment, the storage case 100 further comprises a first battery 140 and a first charging structure 150. The first battery 140 is mounted in the mounting cavity 112 and is electrically connected to the ultraviolet lamp 130 through the circuit board 120. The first charging structure 150 is exposed on an outer sidewall of the base 110. The first charging structure 150 is electrically connected to the first battery 140 through the circuit board 120 to charge the first battery 140.

In the embodiment, the first battery 140 is disposed inside the storage case 100, and the first battery 140 provides electric energy for the ultraviolet lamp 130, so that the ultraviolet lamp 130 is capable of emitting the ultraviolet rays. Therefore, when the user uses the storage case 100 to sterilize the suction massager 200, no wire needs to be connected, making the storage case very convenient to use. After the first battery 140 is fully charged, the first battery 140 is allowed to charge the ultraviolet lamp 130 multiple times. In order to charge the first battery 140, the storage case 100 of the embodiment comprises the first charging structure 150 exposed on the outer sidewall of the base 110, and the first charging structure 150 is electrically connected to the first battery 140 through the circuit board 120.

Specifically, the first charging structure 150 is configured to connect to an external charger to charge the first battery 140. There are many specific implementations of the first charging structure 150. For instance, the first charging structure 150 is charging contacts, a TYPE-C interface, a Micro-USB interface, etc., as long as the first battery 140 is allowed to be charged through the first charging structure 150, which is not limited thereto and is allowed to be reasonably adjusted by hose skilled in the art.

As shown in FIGS. 2 and 3, in one specific embodiment, the storage case 100 further comprises second charging structures 160. A first end of each of the second charging structures 160 is exposed on the groove wall of the storage groove 111, and a second end of each of the second charging structures 160 is electrically connected to the first battery 140 through the circuit board 120, so that the second charging structures 160 are allowed to charge the suction massager 200.

In the embodiment, when using the storage case 100 to store the suction massager 200, the storage case 100 also charges the suction massager 200, so that every time the user takes out the suction massager 200 from the storage case 100, the suction massager 200 is charged and has sufficient power. Thus, the user does not need to charge the suction massager 200 separately, which is very convenient to use and provides an excellent user experience.

Figure 5:
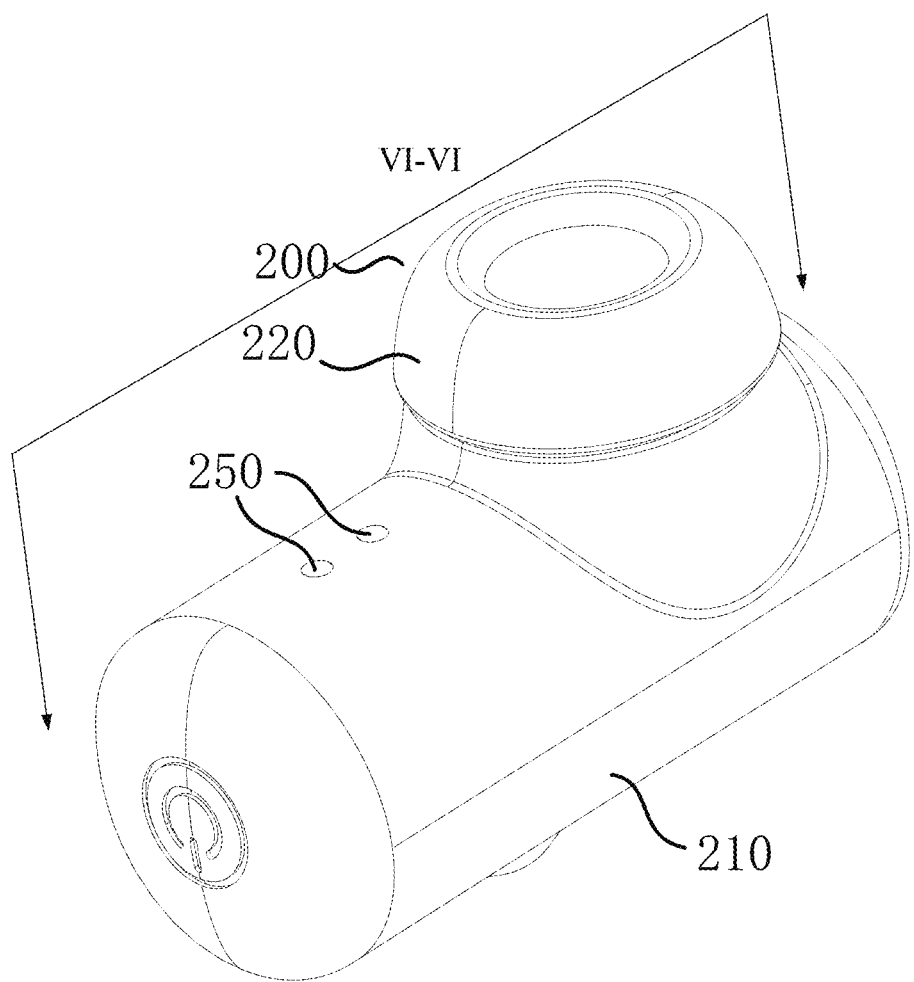
FIG. 5 is a perspective schematic diagram of the suction massager according to one embodiment of the present disclosure.

As shown in FIGS. 2 and 5, in one specific embodiment, the second charging structures 160 are spring pins. In this way, the second charging structures 160 are able to charge the suction massager 200 as long as the second charging structures 160 contact charging contacts on the suction massager 200, which makes the suction massager 200 very convenient to use. Further, rather than aligning and inserting a plug into a socket for charging, the second charging structures 160 directly charge the suction massager 200 when the suction massager 200 is placed in the store groove.

Of course, it is understandable that the second charging structures 160 may also be a TYPE-C interface, a Micro-USB interface, etc.

As shown in FIG. 3, in one specific embodiment, the storage case 100 further comprises third charging structures 170. A first end of each of the third charging structures 170 is exposed on the outer sidewall of the base 110, and a second end of each of the third charging structures 170 is electrically connected to the first battery 140 through the circuit board 120, so that the third charging structures 170 are allowed to charge an external electronic device.

In the embodiment, the storage case 100 is also functioned as a power bank to charge the external electronic device, which is very suitable for the user who need to travel or go on business trips.

In some embodiments, a control module is disposed on the circuit board 120, and the control module is configured to control the ultraviolet lamp 130 to work for a predetermined time when the second charging structures 160 charge the suction massager 200.

Specifically, the predetermined time may be a default time length predetermined at a factory, the predetermined time may be selected from a plurality of time lengths predetermined at the factory by the user, or the predetermined time may be a customized time length set by the user, which is not specifically limited thereto.

In some embodiments, the storage case 100 further comprises a travel switch or an electromagnetic induction switch. The travel switch or the electromagnetic induction switch is electrically connected to the ultraviolet lamp 130. After the travel switch or the electromagnetic induction switch is triggered, the ultraviolet lamp 130 works for a predetermined time. The travel switch or the electromagnetic induction switch is triggered when the suction massager 200 is accommodated in the storage case 100.

In the embodiment, the user only needs to put the suction massager 200 into the storage groove 111, and the ultraviolet lamp 130 may automatically turn on, which is very convenient to use.

As shown in FIGS. 1 and 3, in one specific embodiment, the storage case 100 further comprises a cover 180, and the cover 180 is detachably, rotatably, or slidably mounted at a groove opening of the storage groove 111 to cover or expose the storage groove 111.

Specifically, the cover 180 is able to cover the storage groove 111, so as to prevent the storage groove 111 and the suction massager 200 accommodated in the storage groove 111 from being polluted by the external environment. After the user finishes using the suction massager 200, the suction massager 200 is placed into the storage groove 111, and then the suction massager 200 is covered by the cover 180. When the user needs to use the suction massager 200, the user only needs to open the cover 180 and take out the suction massager 200 accommodated in the storage groove 111, which is very convenient to use.

In addition, the storage case facilitates the user to hide the suction massager 200 well and avoids embarrassment and discomfort caused by the suction massager 200 being unnecessarily exposed to the sight of others.

The present disclosure provides a massager system 1000. As shown in FIGS. 3-7, the massager system 1000 comprises a suction massager 200 and the storage case 100 mentioned above. The suction massager 200 comprises a main body 210 and a flexible massage piece mounted on the main body 210. The storage groove 111 is configured to accommodate the suction massager 200.

The suction massager 200 is an electronic product that is placed on the skin of the user to make the user feel like being sucked. The flexible massage piece 220 mounted on the main body 210 is configured to contact the skin of the user.

In the embodiment of the present disclosure, the storage case stores the suction massager 200 while sterilizing the suction massager 200 through the ultraviolet rays, which effectively reduces the number of the bacteria on the suction massager 200, thereby ensuring the physical health of the user.

Furthermore, a shape of the storage case 100 is matched with a shape of the suction massager 200, and the ultraviolet lamp 130 of the storage case 100 faces the flexible massage piece of the suction massager 200.

As shown in FIG. 5, in one specific embodiment, the shape of the storage case 100 is matched with the shape of the suction massager 200, so the ultraviolet lamp 130 of the storage case 100 directly faces the flexible massage piece 220 of the suction massager 200.

Specifically, when the user uses the suction massager 200, body fluids may flow to the flexible massage piece 220 of the suction massager 200, so the flexible massage piece 220 is more likely to breed bacteria. The shape of the storage compartment 100 in the embodiment is matched with the suction massager 200, so the suction massager 200 does not shake when being placed in the storage case 100. The ultraviolet lamp 130 of the storage case 100 directly faces the flexible massage piece 220 of the suction massager 200, so that the flexible massage piece 220 is well sterilized by the ultraviolet rays emitted by the ultraviolet lamp 130.

Figure 6:
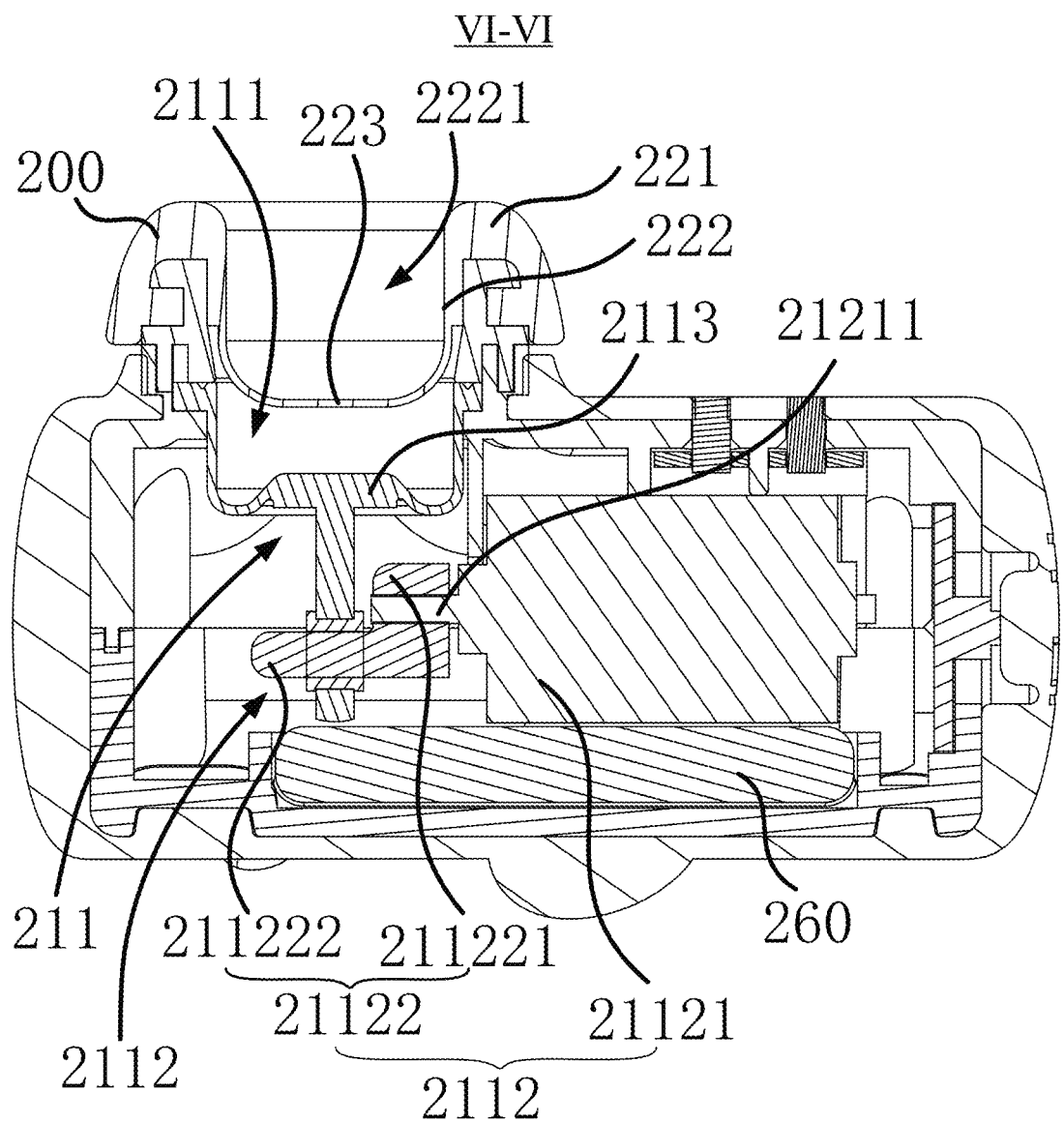
FIG. 6 is a cross-sectional schematic diagram of the suction massager shown in FIG. 5 taken along a line VI-VI, according to one embodiment of the present disclosure.

As shown in FIGS. 5 and 6, in one specific embodiment, the main body 210 comprises a pressure field generating mechanism 211. The pressure field generating mechanism 211 comprises a chamber 2111, a power assembly 2112, and an output piece 2113. The output piece 2113 is configured as at least a part of a chamber wall of the chamber 2111. The power assembly 2112 is connected to the output piece 2113, and the power assembly 2112 is configured to push the output piece 2113 to move or deform, so as to change a volume of the chamber 2111. The chamber 2111 defines a second opening 21111.

The flexible massage piece 220 comprises a contact portion 221 and a recessed portion 222. The contact portion 221 is configured to contact a human body. The recessed portion 222 is disposed on a central position of the contact portion. The recessed portion 222 defines a recessed cavity 2221. A flexible film 223 is disposed on a bottom portion of the recessed cavity 2221. The flexible massage piece 220 is mounted on the second opening 21111 of the chamber 2111. The recessed portion 222 extends into the chamber 2111 from the second opening 21111 of the chamber 2111 to seal the chamber 2111. When the volume of the chamber 2111 changes, a pressure difference formed on two sides of the flexible film 223 causes the flexible film 223 to deform to change the volume of the recessed cavity 2221.

A working principle of the suction massager 200 in the embodiment is as follows.

The power assembly 2112 pushes the output piece 2113 to move or deform, so that the negative pressure is formed in the chamber 2111 that is sealed. At this time, the pressure difference is formed on the two sides of the flexible film 223, causing the flexible film 223 to deform. When the flexible massage piece 220 is placed on the skin, the recessed cavity 2221 generates the negative pressure due to the deformation of the flexible massage piece 220, which brings the user the feeling of being sucked and realize massage for the user.

Specifically, in the embodiment, the recessed cavity 2221 and the chamber 2111 are isolated, that is, the recessed cavity 2221 is not connected to the chamber 2111. Therefore, even when the suction massager 200 is in use and the body fluids flow to the flexible massager piece 220, the body fluids are limited in the recessed cavity 2221 of the flexible massage piece 220 and do not flow to the output piece 2113. Therefore, the suction massager 200 is much more convenient and easier to clean, which avoids adverse effects on the physical health of the user due to unclean cleaning of the suction massager 200 to a certain extent.

As shown in FIGS. 5 and 6, in one specific embodiment, the flexible massage piece 220 is detachably mounted on the second opening 21111 of the chamber 2111. In this way, the user is allowed to regularly replace the flexible massage piece 220. Further, since the flexible massage piece 220 is detachable, it is more convenient and easier to clean.

In addition, since the flexible massage piece 220 is detachable, manufacturers can design different flexible massage pieces 220 of different shapes and sizes for the different users to replace to meet different preferences of different users.

It is worth mentioning that there are many ways to realize detachable connection of the flexible massage pieces 220, such as buckles, magnetic adsorption, etc., which is not limited thereto and is determined by those skilled in the art.

As shown in FIGS. 5 and 6, in one specific embodiment, the suction massager 200 further comprises a third battery 260 and fifth charging structures 250, and the third battery 260 is electrically connected to the power assembly 2112 to provide the electric energy to the power assembly 2112. The fifth charging structures 250 are exposed on a surface of the suction massager 200 and is electrically connected to the third battery 260. The fifth charging structures 250 are configured to connect to the second charging structures 160 to charge the third battery 260.

In the embodiment, when using the storage case 100 to store the suction massager 200, the storage case 100 also charges the suction massager 200, so that every time the user takes out the suction massager 200 from the storage case 100, the suction massager 200 is charged and has sufficient power. Thus, the user does not need to charge the suction massager 200 separately, which is very convenient to use and provides an excellent user experience.

As shown in FIGS. 2 and 5, in one specific embodiment, the fifth charging structures 250 are the charging contacts, and the second charging structures 160 are the spring pins. In this way, as long as the fifth charging structures 250 contact the second charging structures 160, the third battery is charged. Rather than aligning and inserting the plug into the socket for charging, the fifth charging structures 250 directly contact the second charging structures 160 for charging the third battery 260.

As shown in FIG. 6, in one specific embodiment, the power assembly 2112 comprises a rotating driving piece 21121 and an eccentric rod 21122. The eccentric rod 21122 comprises a mounting portion 211221 and an eccentric portion 211222. The mounting portion 211221 is mounted on the rotating shaft 211211 of the rotating driving piece 21121. A central axis of the eccentric portion 211222 is spaced apart from a central axis of the rotating shaft 211211. The output piece 2113 is connected to the eccentric portion 211222.

Specifically, the rotating driving piece 21121 is configured to drive the eccentric rod 21122 to rotate. Since the central axis of the eccentric portion 211222 of the eccentric rod 21122 is spaced apart from the central axis of the rotating shaft 211211 of the rotating driving piece 21121, and the output piece 2113 is connected to the eccentric portion 211222, when the rotating driving piece 21121 drives the eccentric rod 21122 to rotate, the eccentric portion 211222 pulls/compress the output piece 2113, thereby forming the negative pressure in the chamber 2111.

Figure 7:
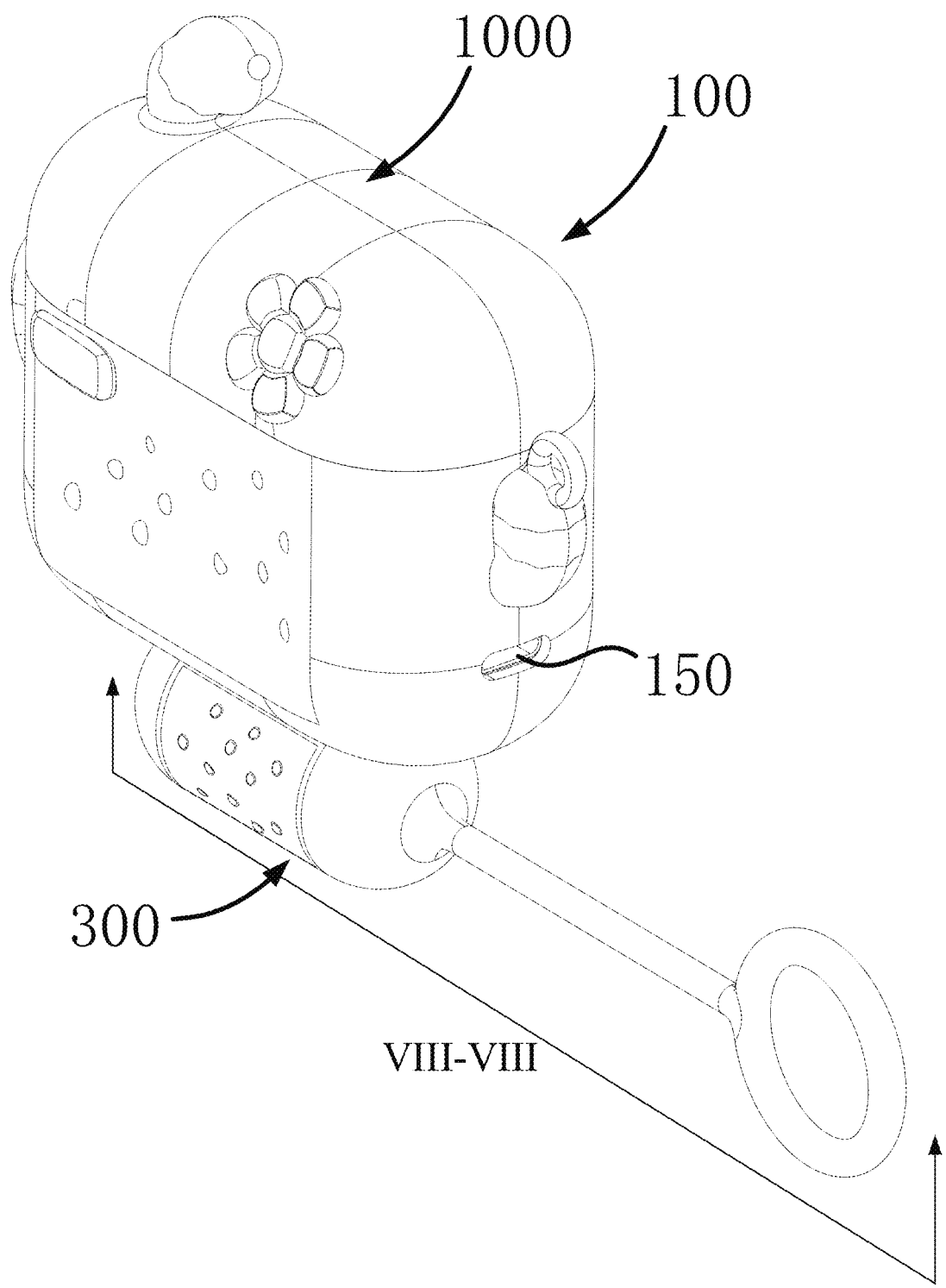
FIG. 7 is a perspective schematic diagram of a massager system according to one embodiment of the present disclosure.

As shown in FIG. 7, in one specific embodiment, the massager system comprises a vibration massager 300. The vibration massager 300 comprises a motor 310 and a vibrator 320 driven by the motor 310. The vibration massager 300 may be placed on the skin of the user to massage the user through vibration.

Figure 8:
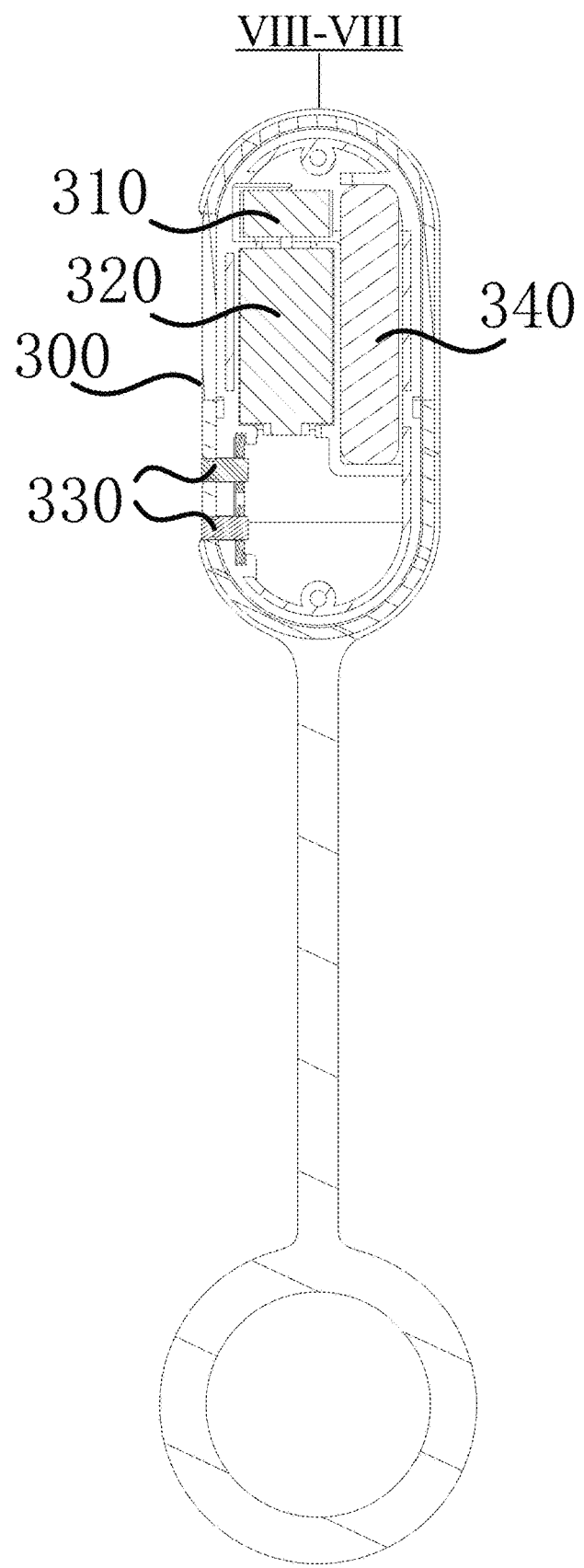
FIG. 8 is a cross-sectional schematic diagram of a vibration massager shown in FIG. 7 taken along a line VIII-VIII, according to one embodiment of the present disclosure.

As shown in FIGS. 7 and 8, in one specific embodiment, the vibration massager 300 comprises a second battery 340 and fourth charging structures 330. The second battery 340 is disposed inside the vibration massager 300 and is electrically connected to the motor 310. The fourth charging structures 330 are exposed on a surface of the vibration massager 300. The fourth charging structures 330 are electrically connected to the second battery 340. The fourth charging structures 330 are connected to the third charging structures 170 of the storage case 100 to charge the second battery 340.

As shown in FIGS. 3 and 8, furthermore, the fourth charging structures 330 are the charging contacts, and the third charging structures 170 are the spring pins. In this way, as long as the fourth charging structures 330 contact the third charging structures 160, the second battery 340 is charged. Rather than aligning and inserting the plug into the socket for charging, the fourth charging structures 330 directly contact the third charging structures 170 for charging the second battery 340.

In one specific embodiment, a first magnetic piece is disposed adjacent to the third charging structures 170, and a second magnetic piece configured to connect to the first magnetic piece is disposed on the vibration massager 300. The first magnetic piece and the second magnetic piece are attracted to each other, so as to ensure that the third charging structures 170 are respectively connected to the fourth charging structures 330, and ensure that the third charging structures 170 and the fourth charging structures 330 are not out of contact due to small external force.

It should be noted that the above embodiments are only used to illustrate the technical solutions of the present disclosure and are not limitations thereof. For those skilled in the art, the technical solutions described in the above embodiments can be modified, or equivalent substitutions can be made on some of the technical features; and all these modifications and substitutions should fall within the protection scope of the claims appended to the present disclosure.

What is claimed is:

1. A storage case, configured to store a suction massager, comprising:
    a base,
    a circuit board,
    an ultraviolet lamp,
        wherein a storage groove is defined in one side of the base; the storage groove is configured to accommodate the suction massager; a mounting cavity is formed in the base; a first opening is defined in a groove wall of the storage groove to communicate the storage groove with the mounting cavity; the circuit board is mounted in the mounting cavity; the ultraviolet lamp is electrically connected to the circuit board; the ultraviolet lamp is mounted at the first opening of the storage groove, so that the ultraviolet lamp emits ultraviolet rays towards the storage groove;
    a first battery, being mounted in the mounting cavity and electrically connected to the ultraviolet lamp through the circuit board; and
    external-device charging structures, wherein a first end of each of the external-device charging structures is exposed on an outer sidewall of the base, and a second end of each of the external-device charging structures is electrically connected to the first battery through the circuit board, so that the external-device charging structures are allowed to charge an external electronic device;
    wherein the storage case further comprises a first charging structure; the first charging structure is exposed on the outer sidewall of the base; the first charging structure is electrically connected to the first battery through the circuit board to charge the first battery; and
    the storage case further comprises second charging structures; a first end of each of the second charging structures is exposed on the groove wall of the storage groove, and a second end of each of the second charging structures is electrically connected to the first battery through the circuit board, so that the second charging structures are allowed to charge the suction massager.

2. The storage case according to claim 1, wherein the second charging structures are spring pins.

3. The storage case according to claim 1, wherein a control module is disposed on the circuit board, and the control module is configured to control the ultraviolet lamp to work for a predetermined time when the second charging structures charge the suction massager.

4. The storage case according to claim 1, wherein the storage case further comprises a travel switch or an electromagnetic induction switch; the travel switch or the electromagnetic induction switch is electrically connected to the ultraviolet lamp; after the travel switch or the electromagnetic induction switch is triggered, the ultraviolet lamp works for a predetermined time; the travel switch or the electromagnetic induction switch is triggered when the suction massager is accommodated in the storage case.

5. A massager system, comprising:
    a suction massager, and
    a storage case;
    wherein the suction massager comprises a main body and a flexible massage piece mounted on the main body;
    wherein the storage case comprises a base, a circuit board, an ultraviolet lamp, a first battery, and external-device charging structures; a storage groove is defined in one side of the base; the storage groove is configured to accommodate the suction massager; a mounting cavity is formed in the base; a first opening is defined in a groove wall of the storage groove to communicate the storage groove with the mounting cavity; the circuit board is mounted in the mounting cavity; the ultraviolet lamp is electrically connected to the circuit board; the ultraviolet lamp is mounted at the first opening of the storage groove, so that the ultraviolet lamp is allowed to emit ultraviolet rays towards the storage groove; and
    the first battery is mounted in the mounting cavity and is electrically connected to the ultraviolet lamp through the circuit board; a first end of each of the external-device charging structures is exposed on an outer sidewall of the base, and a second end of each of the external-device charging structures is electrically connected to the first battery through the circuit board, so that the external-device charging structures are allowed to charge an external electronic device;
    wherein the storage case further comprises a first charging structure; the first charging structure is exposed on the outer sidewall of the base; the first charging structure is electrically connected to the first battery through the circuit board to charge the first battery; and
    the storage case further comprises second charging structures; a first end of each of the second charging structures is exposed on the groove wall of the storage groove, and a second end of each of the second charging structures is electrically connected to the first battery through the circuit board, so that the second charging structures are allowed to charge the suction massager.

6. The massager system according to claim 5, wherein a shape of the storage case is matched with a shape of the suction massager, and the ultraviolet lamp of the storage case faces the flexible massage piece of the suction massager.

7. The massager system according to claim 6, wherein the main body comprises a pressure field generating mechanism; the pressure field generating mechanism comprises a chamber, a power assembly, and an output piece; the output piece is configured as at least a part of a chamber wall of the chamber; the power assembly is connected to the output piece, and the power assembly is configured to push the output piece to move or deform, so as to change a volume of the chamber; the chamber defines a second opening;

wherein the flexible massage piece comprises a contact portion and a recessed portion; the contact portion is configured to contact a human body; the recessed portion is disposed on a central position of the contact portion; the recessed portion defines a recessed cavity; a flexible film is disposed on a bottom portion of the recessed cavity; the flexible massage piece is mounted on the second opening of the chamber; the recessed portion extends into the chamber from the second opening of the chamber to seal the chamber; when the volume of the chamber changes, a pressure difference formed on two sides of the flexible film causes the flexible film to deform to change the volume of the recessed cavity.

8. A massager system, comprising:

a suction massager, a storage case, and a vibration massager;

wherein the suction massager comprises a main body and a flexible massage piece mounted on the main body;

wherein the storage case comprises a base, a circuit board, and an ultraviolet lamp; a storage groove is defined in one side of the base; the storage groove is configured to accommodate the suction massager; a mounting cavity is formed in the base; a first opening is defined in a groove wall of the storage groove to communicate the storage groove with the mounting cavity; the circuit board is mounted in the mounting cavity; the ultraviolet lamp is electrically connected to the circuit board; the ultraviolet lamp is mounted at the first opening of the storage groove, so that the ultraviolet lamp is allowed to emit ultraviolet rays towards the storage groove;

wherein the storage case further comprises a first battery and a first charging structure; the first battery is mounted in the mounting cavity and is electrically connected to the ultraviolet lamp through the circuit board; the first charging structure is exposed on an outer sidewall of the base; the first charging structure is electrically connected to the first battery through the circuit board to charge the first battery;

wherein the storage case further comprises second charging structures; a first end of each of the second charging structures is exposed on the groove wall of the storage groove, and a second end of each of the second charging structures is electrically connected to the first battery through the circuit board, so that the second charging structures are allowed to charge the suction massager;

wherein the vibration massager comprises a motor, a vibrator driven by the motor, and a second battery disposed therein;

wherein the storage case further comprises third charging structures, a first end of each of the third charging structures is exposed on the outer sidewall of the base, and a second end of each of the third charging structures is electrically connected to the first battery through the circuit board, so that the third charging structures are allowed to charge an external electronic device;

wherein the second battery is electrically connected to the motor; fourth charging structures are exposed on a surface of the vibration massager; the fourth charging structures are electrically connected to the second battery; the fourth charging structures are connected to the third charging structures of the storage case to charge the second battery.

\* \* \* \* \*